(12) United States Patent
Ikeda

(10) Patent No.: US 9,119,400 B2
(45) Date of Patent: *Sep. 1, 2015

(54) METHOD OF CONTROLLING WEEDS

(75) Inventor: Hajime Ikeda, Kobe (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 75 days.

This patent is subject to a terminal disclaimer.

(21) Appl. No.: 13/018,470

(22) Filed: Feb. 1, 2011

(65) Prior Publication Data

US 2011/0190131 A1 Aug. 4, 2011

(30) Foreign Application Priority Data

Feb. 4, 2010 (JP) ................. 2010-022919

(51) Int. Cl.
*A01N 43/84* (2006.01)
*A01N 43/80* (2006.01)
*A01N 41/10* (2006.01)

(52) U.S. Cl.
CPC ............... *A01N 43/84* (2013.01); *A01N 41/10* (2013.01); *A01N 43/80* (2013.01)

(58) Field of Classification Search
CPC ....... A01N 43/84; A01N 43/80; A01N 35/06; A01N 41/02; A01N 41/10
USPC ....................................... 504/130
See application file for complete search history.

(56) References Cited

U.S. PATENT DOCUMENTS

| 4,640,707 | A | 2/1987 | Nagano et al. |
| 6,534,444 | B1 | 3/2003 | Sievernich et al. |
| 2003/0130120 | A1* | 7/2003 | Ziemer et al. ................. 504/105 |
| 2004/0033897 | A1 | 2/2004 | Haas |
| 2010/0197503 | A1* | 8/2010 | Hawkes et al. ............... 504/348 |
| 2011/0065579 | A1* | 3/2011 | Sievernich et al. ........... 504/128 |

FOREIGN PATENT DOCUMENTS

| DE | 19834627 A1 | 12/1998 |
| WO | 00/27203 A1 | 5/2000 |
| WO | 00/74488 A1 | 12/2000 |
| WO | 01/94339 A1 | 12/2001 |

* cited by examiner

*Primary Examiner* — John Pak
*Assistant Examiner* — Andriae M Holt
(74) *Attorney, Agent, or Firm* — Birch, Stewart, Kolasch & Birch, LLP

(57) ABSTRACT

A method of controlling weeds in a soybean or cotton field, which comprises the step of applying one or more 4-hydroxyphenylpyruvate dioxygenase inhibitory active compounds and flumioxazin in an effective amount to weeds in a soybean or cotton field, or a place where weeds would grow, said 4-hydroxyphenylpyruvate dioxygenase inhibitory active compounds being selected from the group consisting of isoxaflutole, mesotrione, sulcotrione, topramezone, pyrasulfotole, tembotrione and bicyclopyrone.

6 Claims, No Drawings

METHOD OF CONTROLLING WEEDS

TECHNICAL FIELD

The present invention relates to a method of controlling weeds.

BACKGROUND ART

A lot of compounds are known as active ingredients of herbicides, as mentioned in U.S. Pat. No. 4,640,707 specification; Crop Protection Handbook 2008, Meister Publishing Company, ISBN:1-892829-20-7; The Pesticide Manual Fourteenth Edition (2006), British Crop Council, ISBN:1-901396-14-2; or Herbicide Handbook Eighth Edition (2002), Weed Science Society of America, ISBN:1-891276-33-6.

SUMMARY OF THE INVENTION

The present invention includes the following.

[1] A method of controlling weeds in a soybean or cotton field, which comprises the step of applying one or more 4-hydroxyphenylpyruvate dioxygenase inhibitory active compounds and flumioxazin in an effective amount to weeds in a soybean or cotton field, or a place where weeds would grow, said 4-hydroxyphenylpyruvate dioxygenase inhibitory active compounds being selected from the group consisting of isoxaflutole, mesotrione, sulcotrione, topramezone, pyrasulfotole, tembotrione and bicyclopyrone.

[2] The method according to [1], wherein the 4-hydroxyphenylpyruvate dioxygenase inhibitory active compound and flumioxazin are applied in a weight ratio of 1:0.025 to 1:1200 (=4-hydroxyphenylpyruvate dioxygenase inhibitory active compound:flumioxazin).

[3] The method according to [1], wherein the 4-hydroxyphenylpyruvate dioxygenase inhibitory active compound and flumioxazin are applied in a weight ratio of 1:0.01 to 1:300 (=4-hydroxyphenylpyruvate dioxygenase inhibitory active compound:flumioxazin).

[4] The method according to [1], wherein the 4-hydroxyphenylpyruvate dioxygenase inhibitory active compound and flumioxazin are applied in a weight ratio of 1:0.08 to 1:40 (=4-hydroxyphenylpyruvate dioxygenase inhibitory active compound:flumioxazin).

[5] The method according to any one of [1] to [4], wherein soybean in the soybean field is transgenic soybean.

[6] The method according to any one of [1] to [4], wherein soybean in the soybean field is herbicide-resistant transgenic soybean.

[7] The method according to any one of [1] to [4], wherein soybean in the soybean field is 4-hydroxyphenylpyruvate dioxygenase inhibitor-resistant transgenic soybean.

[8] The method according to any one of [1] to [4], wherein soybean in the soybean field is soybean having one or more genes selected from the group consisting of a gene encoding 4-hydroxyphenylpyruvate dioxygenase exhibiting resistance to a 4-hydroxyphenylpyruvate dioxygenase inhibitor, a gene encoding an enzyme capable of synthesizing homogentisic acid even when 4-hydroxyphenylpyruvate dioxygenase is inhibited by a 4-hydroxyphenylpyruvate dioxygenase inhibitor, a gene capable of excessively expressing 4-hydroxyphenylpyruvate dioxygenase, and a gene encoding prephenate dehydrogenase.

[9] The method according to any one of [1] to [4], wherein cotton in the cotton field is transgenic cotton.

[10] The method according to any one of [1] to [4], wherein cotton in the cotton field is herbicide-resistant transgenic cotton.

[11] The method according to any one of [1] to [4], wherein cotton in the cotton field is 4-hydroxyphenylpyruvate dioxygenase inhibitor transgenic cotton.

[12] The method according to any one of [1] to [4], wherein cotton in the cotton field is cotton having one or more genes selected from the group consisting of a gene encoding 4-hydroxyphenylpyruvate dioxygenase exhibiting resistance to a 4-hydroxyphenylpyruvate dioxygenase inhibitor, a gene encoding an enzyme capable of synthesizing homogentisic acid even when 4-hydroxyphenylpyruvate dioxygenase is inhibited by a 4-hydroxyphenylpyruvate dioxygenase inhibitor, a gene capable of excessively expressing 4-hydroxyphenylpyruvate dioxygenase, and a gene encoding prephenate dehydrogenase.

[13] A herbicidal composition comprising pyrasulfotole and flumioxazin.

[14] A herbicidal composition comprising tembotrione and flumioxazin.

Effects of the Invention

According to the present invention, weeds in a soybean or cotton field can be effectively controlled.

MODE FOR CARRYING OUT THE INVENTION

The method of the present invention includes the step of applying one or more 4-hydroxyphenylpyruvate dioxygenase inhibitory active compounds (hereinafter referred to as a HPPD inhibitory active compound) and flumioxazin in an effective amount to weeds in the soybean or cotton field, or the place where weeds would grow.

Here, each of 4-hydroxyphenylpyruvate dioxygenase inhibitory active compounds is selected from the group consisting of isoxaflutole, mesotrione, sulcotrione, topramezone, pyrasulfotole, tembotrione and bicyclopyrone.

Isoxaflutole has a chemical name of (5-cyclopropyl-1,2-oxazol-4-yl)(α,α,α-trifluoro-2-mesyl-p-tolyl)methanone.

Mesotrione has a chemical name of 2-(4-mesyl-2-nitrobenzoyl)cyclohexane-1,3-dione.

Sulcotrione has a chemical name of 2-(2-chloro-4-mesylbenzoyl)cyclohexane-1,3-dione.

Topramezone has a chemical name of [3-(4,5-dihydro-1,2-oxazole-3-yl)-4-mesyl-o-tolyl](5-hydroxy-1-methylpyrazol-4-yl)methanone.

Pyrasulfotole has a chemical name of (5-hydroxy-1,3-dimethylpyrazol-4-yl)(α,α,α-trifluoro-2-mesyl-p-tolyl)methanone.

Tembotrione has a chemical name of 2-{2-chloro-4-mesyl-3-[(2,2,2-trifluoroethoxy)methyl]benzoyl}cyclohexane-1,3-dione.

Bicyclopyrone has a chemical name of 4-hydroxy-3-{2-[(2-methoxyethoxy)methyl]-6-(trifluoromethyl)-3-pyridylcarbonyl}bicyclo[3.2.1]oct-3-en-2-one.

Isoxaflutole, mesotrione, sulcotrione, topramezone, pyrasulfotole, tembotrione and bicyclopyrone are respectively described in Crop Protection Handbook 2008, Meister Publishing Company, ISBN:1-892829-20-7; The Pesticide Manual Fourteenth Edition (2006), British Crop Council, ISBN:1-901396-14-2; Herbicide Handbook Eighth Edition (2002), Weed Science Society of America, ISBN:1-891276-33-6; Compendium of Pesticide Common Names (http://www.alanwood.net/pesticides/); Pamphlet of International Publication WO 2001/094339 and the like, and can be produced by a known production method. Also, commercially available products can be purchased.

All of isoxaflutole, mesotrione, sulcotrione, topramezone, pyrasulfotole, tembotrione and bicyclopyrone are 4-hydroxyphenylpyruvate dioxygenase inhibitory active compounds, and inhibit 4-hydroxyphenylpyruvate dioxygenase (EC 1.13.11.27) which catalyzes a reaction of converting p-hydroxyphenylpyruvic acid into homogentisic acid thereby indirectly inhibiting biogenesis of carotenoid, resulting in death of plants. Such an action mechanism is well known and is described, for example, in Kenneth E. Paletta (2000) The mode of action of Isoxaflutole: a case study of an emerging target site. Herbicides and their Mechanisms of Action, 215-238 CRC Press, ISBN: 1-84127-109-8.

Flumioxazin has a chemical name of N-(7-fluoro-3,4-dihydro-3-oxo-4-prop-2-ynyl-2H-1,4-benzoxazine-6-yl)cyclohex-1-ene-1,2-dicarboxamide. Flumioxazin is a compound described in U.S. Pat. No. 4,640,707 and the like and can be produced by the method described in the publication.

In the method of the present invention, examples of a typical combination of a HPPD inhibitory active compound and flumioxazin include the following combinations:
  isoxaflutole and flumioxazin,
  mesotrione and flumioxazin,
  sulcotrione and flumioxazin,
  topramezone and flumioxazin,
  pyrasulfotole and flumioxazin,
  tembotrione and flumioxazin, and
  bicyclopyrone and flumioxazin.

Such combinations are preferably pyrasulfotole and flumioxazin; tembotrione and flumioxazin; isoxaflutole and flumioxazin; or mesotrione and flumioxazin, and more preferably isoxaflutole and flumioxazin; as well as mesotrione and flumioxazin.

A herbicide composition composed of pyrasulfotole and flumioxazin, and a herbicide composition composed of tembotrione and flumioxazin are novel compositions.

In the method of the present invention, a ratio of a HPPD inhibitory active compound to flumioxazin to be applied is usually from 1:0.01 to 1:1200, preferably from 1:0.025 to 1:1200, more preferably from 1:0.01 to 1:300, still more preferably from 1:0.08 to 1:40, and particularly preferably from 50:1 to 1:20.

In the method of the present invention, a HPPD inhibitory active compound and flumioxazin are applied in an effective amount to a soybean or cotton field. In the present description, the effective amount means the total amount of the HPPD inhibitory active compound and flumioxazin, in which amount weeds can be controlled. In the control method, each amount of the HPPD inhibitory active compound and flumioxazin may be such an amount that weeds cannot be controlled at use of any one compound only.

In the method of the present invention, the application amount of the HPPD inhibitory active compound and flumioxazin, namely, the effective amount is usually from 1 to 1,000 g, preferably from 15 to 1,000 g, and more preferably from 30 to 500 g, in terms of the total amount of the HPPD inhibitory active compound and flumioxazin, per 10,000 m$^2$ of the soybean or cotton field.

In the method of the present invention, the HPPD inhibitory active compound and flumioxazin may be mixed, namely, used as a mixture thereof, or may be used in combination, namely, used together without mixing.

In the control method, there is no limitation on the form of the HPPD inhibitory active compound and flumioxazin. However, they may be preferably formulations, respectively.

There is no limitation of the form of the formulation, and examples thereof include an emulsifiable concentrate, a wettable powder, a granular wettable powder, a granular water soluble powder, a flowable formulation (e.g., an aqueous suspension, or an aqueous emulsion), a dust, a granule, an oil solution and a microcapsule. In the case these formulations are respectively used as the HPPD inhibitory active compound and flumioxazin, the formulation may be applied after dilution.

The respective formulations of the HPPD inhibitory active compound and flumioxazin can be produced by a known method.

In the method of the present invention, the HPPD inhibitory active compound and flumioxazin are applied to a soybean or cotton field, specifically, weeds in the soybean or cotton field, or the place where weeds would grow. Examples of the application to weeds include an application to weeds per se and an application to the soil after invasion of weeds. Examples of the treatment to the place where weeds would grow include an application to a surface of the soil before invasion of weeds.

In the method of the present invention, examples of the method of applying a HPPD inhibitory active compound and flumioxazin to weeds in the soybean or cotton field, or the place where weeds would grow include:
  a method in which a formulation of a HPPD inhibitory active compound and a formulation of flumioxazin are respectively diluted with water and the respective water dilutions are mixed, and then the mixed water dilution is applied to weeds in the soybean or cotton field, or the place where weeds would grow;
  a method in which a formulation of a HPPD inhibitory active compound and a formulation of flumioxazin are respectively diluted with water, the respective water dilutions are sequentially applied to weeds in the soybean or cotton field, or the place where weeds would grow (there is no limitation on the order of application of the respective water dilutions);
  a method in which a formulation of a HPPD inhibitory active compound and a formulation of flumioxazin are mixed and the mixture is diluted with water, and then the water dilution of the mixture is applied to weeds in the soybean or cotton field, or the place where weeds would grow; and
  a method in which a formulation of a HPPD inhibitory active compound and a formulation of flumioxazin are sequentially applied to weeds in the soybean or cotton field, or the place where weeds would grow (there is no limitation on the order of application of the formulation).

In the method of the present invention, the HPPD inhibitory active compound and flumioxazin may be applied before sowing seeds of soybean or cotton, after sowing and before emergence of soybean or cotton, and after emergence of soybean or cotton.

Examples of the aspect of the method of applying a HPPD inhibitory active compound and flumioxazin in the method of the present invention include:
  a method which comprises spraying over a surface of the soil before sowing seeds of soybean or cotton and before weed emergence;
  a method which comprises spraying over a surface of the soil before sowing seeds of soybean or cotton and after weed emergence;
  a method which comprises spraying over weeds before sowing seeds of soybean or cotton and after weed emergence;
  a method which comprises spraying over a surface of the soil after sowing seeds of soybean or cotton and before emergence of soybean or cotton, and before weed emergence;

a method which comprises spraying over a surface of the soil after sowing seeds of soybean or cotton and before emergence of soybean or cotton, and after weed emergence;

a method which comprises spraying over weeds after sowing seeds of soybean or cotton and before emergence of soybean or cotton, and after weed emergence;

a method which comprises spraying over a surface of the soil after emergence of soybean or cotton and before emergence of weeds;

a method which comprises spraying over a surface of the soil after emergence of soybean or cotton and after emergence of weeds; and a method which comprises spraying over weeds after emergence of soybean or cotton and after emergence of weeds.

In the method of the present invention, soybean in the soybean field may be transgenic soybean, and cotton in the cotton field may be transgenic cotton.

Examples of the transgenic soybean and transgenic cotton include herbicide-resistant transgenic soybean and herbicide-resistant transgenic cotton, respectively.

Examples of the herbicide the resistance of which has been provided by a herbicide-resistant gene include 4-hydroxyphenylpyruvate dioxygenase (hereinafter refer to as HPPD) inhibitors such as isoxaflutole; acetolactate synthase (hereinafter refer to as ALS) inhibitors such as imazethapyr and thifensulfuron-methyl; 5-enolpyruvylshikimate-3-phosphate synthase (hereinafter refer to as EPSP) inhibitors such as glyphosate; glutamine synthase inhibitors such as glufosinate; auxin-type herbicides such as 2,4-D and dicamba; protoporphyrinogen IX oxidase-inhibiting herbicides such as flumioxazin and fomesafen; and herbicides such as bromoxynil.

Typical example of the transgenic soybean includes 4-hydroxyphenylpyruvate dioxygenase inhibitor-resistant transgenic soybean. Typical example of the transgenic cotton includes 4-hydroxyphenylpyruvate dioxygenase inhibitor-resistant transgenic cotton.

The gene in transgenic soybean and transgenic cotton include one or more genes selected from the group consisting of a gene encoding 4-hydroxyphenylpyruvate dioxygenase exhibiting resistance to a 4-hydroxyphenylpyruvate dioxygenase inhibitor, a gene encoding an enzyme capable of synthesizing homogentisic acid even when 4-hydroxyphenylpyruvate dioxygenase is inhibited by a 4-hydroxyphenylpyruvate dioxygenase inhibitor, a gene capable of excessively expressing 4-hydroxyphenylpyruvate dioxygenase, and a gene encoding prephenate dehydrogenase.

Examples of the transgenic soybean and transgenic cotton include soybean and cotton cultivars provided with resistance to glyphosate, which have been already on the market under the trade names of RoundupReady (registered trademark), Agrisure (registered trademark) GT and Glytol (registered trademark). Examples of the transgenic soybean and transgenic cotton include soybean and cotton cultivars provided with resistance to glufosinate, which have been already on the market under the trade name of LibertyLink (registered trademark). Examples of the transgenic cotton include cotton cultivars provided with resistance to bromoxynil, which have been already on the market under the trade name of BXN. Examples of the transgenic soybean include soybean cultivars provided with resistance to both glyphosate and an ALS inhibitor, which are laid open under the trade names of Optimum (registered trademark) and GAT (registered trademark).

Examples of the plants provided with resistance to an acetyl CoA carboxylase inhibitor are described in Proc. Natl. Acad. Sci. USA), Vol. 87, pp. 7175-7179 (1990) or the like. Also, mutated acetyl CoA carboxylase, which is resistant to an acetyl CoA carboxylase inhibitor, is reported in the Weed Science, Vol. 53, pp. 728-746 (2005) or the like. The plants provided with resistance to an acetyl CoA inhibitor can be fabricated by introducing such a mutated acetyl CoA carboxylase gene into a crop by means of genetic recombination technology, or by introducing resistance-providing mutation into acetyl CoA carboxylase of the crop.

Further, by introducing base substitution mutagenesis nucleic acid into a plant cell and inducing site-specific amino acid substitution mutation to a plant acetyl CoA carboxylase gene and an ALS gene, the technology represented by chimeraplasty technology (Gura T., 'Repairing the Genome's Spelling Mistakes', Science 285: 316-318 (1999)), plants provided with resistance to an acetyl CoA carboxylase inhibitor and an ALS inhibitor are fabricated.

By introducing a degrading enzyme of dicamba, which contains dicamba monooxygenase isolated from Pseudomonas maltophilia, crops such as soybean provided with resistance to dicamba can be fabricated (Behrens et al. 2007 Dicamba Resistance: Enlarging and Preserving Biotechnology-Based Weed Management Strategies. Science 316:1185 to 1188).

By introducing gene encoding aryloxyalkanoate dioxygenase, crops resistant to both herbicide systems of phenoxy acid herbicides such as 2,4-D, MCPA, dichlorprop and mecoprop, and aryloxyphenoxypropionic acid herbicides such as quizalofop, haloxyfop, fluazifop, diclofop, fenoxaprop, metamifop, cyhalofop and clodinafop can be fabricated (WO2005/107437, WO2007/053482, WO2008/141154).

By introducing a gene encoding HPPD which exhibits resistance to a HPPD inhibitor, plants resistant to the HPPD inhibitor can be fabricated (US2004/0058427). By introducing a gene capable of synthesizing homogentisic acid as a product of HPPD through another metabolic pathway even when HPPD is inhibited by a HPPD inhibitor, thus making it possible to fabricate plants which exhibits resistance to the HPPD inhibitor (WO02/036787). By introducing a gene capable of excessively expressing HPPD, HPPD is produced in the amount which does not exerts an adverse influence on the growth of plants even in the presence of a HPPD inhibitor, thus making it possible to fabricate plants which exhibit resistance to the HPPD inhibitor (WO96/38567). By introducing the aforementioned gene capable of excessively expressing HPPD and also introducing a gene encoding prephenate dehydrogenase so as to increase the production amount of p-hydroxyphenylpyruvic acid as a substrate of HPPD, thus making it possible to fabricate plants which exhibits resistance to the HPPD inhibitor (Rippert P et. al. 2004 Engineering plant shikimate pathway for production of tocotrienol and improving herbicide resistance. Plant Physiol. 134:92-100).

Examples of the method of providing crops with resistance to an herbicide include methods of introducing a gene described in WO98/20144, WO2002/46387 or US2005/0246800.

The transgenic soybean and transgenic cotton also include soybean and cotton which made it possible to synthesize selective toxins known as genus *Bacillus*, using genetic recombination technology.

Examples of the toxins expressed in such transgenic soybean and transgenic cotton include insecticidal proteins derived from *Bacillus cereus* and *Bacillus popilliae*; δ-endotoxins derived from *Bacillus thuringiensis*, e.g., Cry1Ab, Cry1Ac, Cry1F, Cry1Fa2, Cry2Ab, Cry3A, Cry3Bb1 and Cry9C, and insecticidal proteins such as VIP1, VIP2, VIP3 and VIP3A; insecticidal proteins derived from nematodes; toxins produced by animals, such as scorpion toxin, spider toxin, bee toxin and insect-specific neurotoxins; filamentous fungi toxins; plant lectins; agglutinin; protease inhibitors such as trypsin inhibitor, serine protease inhibitor, patatin, cystatin and papain inhibitor; ribosome-inactivating proteins (RIP) such as ricin, corn-RIP, abrin, rufin, sapolin and briodin; steroid metabolic enzymes such as 3-hydroxysteroid oxidase, ecdysteroid-UDP-glucosyltransferase and cholesterol oxidase; ecdysone inhibitor; HMG-COA reductase; ion channel inhibitors such as sodium channel and calcium channel inhibitors; juvenile hormone esterase; diuretic hormone acceptors; stilbene synthetase; bibenzyl synthetase; chitinase; and glucanase.

The toxins expressed in such transgenic soybean and transgenic cotton include δ-endotoxin proteins such as Cry1Ab, Cry1Ac, Cry1F, Cry1Fa2, Cry2Ab, Cry3A, Cry3Bb1, Cry9C, Cry34Ab and cry35Ab, hybrid toxins of insecticidal proteins such as VIP1, VIP2, VIP3 and VIP3A, partially deficient toxins, and modified toxins. The hybrid toxins are fabricated by a novel combination of the different domains of such proteins, using genetic recombination technology. There is known, as a partially deficient toxin, Cry1Ab in which a part of amino acid sequence is deficient. In modified toxins, one or more amino acids of a natural toxin are replaced. Examples of such toxins and transgenic plants capable of synthesizing such toxins are described in EP-A-0 374 753, WO93/07278, WO95/34656, EP-A-0 427 529, EP-A-451 878, and WO03/052073. The toxins contained in such transgenic plants impart resistance to insect pests of Coleoptera, insect pests of Diptera and insect pests of Lepidoptera to the plants.

It has already been known that there are transgenic soybean and transgenic cotton containing one or more insecticidal pest-resistant genes and expressing one or more toxins. Some of them are commercially available. Examples of such transgenic soybean and transgenic cotton include Bollgard (registered trademark) I (cotton cultivar expressing a Cry1Ac toxin), Bollgard (registered trademark) II (cotton cultivar expressing Cry1Ab and Cry2Ab toxins) and VIPCOT (registered trademark) (cotton cultivar expressing a VIP toxin).

Also, crops provided with resistance to nematodes and aphid by a classical breeding method are known, and examples thereof include soybean having a Rag1 (Resistance Aphid Gene 1) gene capable of imparting resistance to aphid introduced thereinto.

The transgenic soybean and transgenic cotton include those provided with a capacity of producing an anti-pathogenic substance having selective activity. As the anti-pathogenic, PR proteins (PRPs, described in EP-A-0 392 225) are known. These anti-pathogenic substances and genetically modified plants producing them are described in EP-A-0 392 225, WO95/33818, and EP-A-0 353 191. Examples of the anti-pathogenic substance expressed by such transgenic plants include ion channel inhibitors such as a sodium channel inhibitor and calcium channel inhibitor (KP1, KP4 and KP6 toxins produced by viruses are known); stilbene synthases; bibenzyl synthases; chitinase; glucanase; PR proteins; and anti-pathogenic substances produced by microorganisms, such as peptide antibiotics, antibiotics having a heterocyclic ring and protein factors (called genes resistant to plant diseases and are described in WO03/000906) involved in plant disease resistance.

The above plants include those provided with useful traits, such as reformed oil component and enhanced amino acid content, by means of genetic recombination technique. The plants are exemplified by VISTIVE (registered trademark) (low linolenic soybean with reduced linolenic acid content).

The plants further include stacked varieties, which are fabricated by combining the above classical herbicidal traits or herbicide resistant genes, insecticidal pest resistant genes, anti-pathogenic substance-producing genes, and useful substances such as reformed oil component and enhanced amino acid content.

According to the method of the present invention, weeds in the soybean or cotton field can be effectively controlled. Examples of weeds, which can be controlled by the method of the present invention, include:

Polygonaceae weeds: *Polygonum convolvulus, Polygonum lapathifolium, Polygonum pensylvanicum, Polygonum persicaria, Polygonum longisetum, Polygonum aviculare Polygonum arenastrum, Polygonum cuspidatum, Rumex japonicus, Rumex crispus, Rumex obtusifolius, Rumex acetosa*

Portulacaceae weeds: *Portulaca oleracea*

Caryophyllaceae weeds: *Stellaria media, Cerastium holosteoides, Cerastium glomeratum, Spergula arvensis*

Chenopodiaceae weeds: *Chenopodium album, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Alternanthera philoxeroides, Alternanthera sessilis*

Papaveraceae weeds: *Papaver rhoeas*

Brassicaceae weeds: *Raphanus raphanistrum, Sinapis arvensis, Capsella bursa-pastoris, Brassica juncea, Descurainia pinnata, Rorippa islandica, Rorippa sylvestris, Thlaspi arvense*

Leguminosae weeds: *Aeschynomene indica, Sesbania exaltata, Cassia obtusifolia, Cassia occidentalis, Desmodium tortuosum, Trifolium repens, Pueraria lobata, Vicia angustifolia*

Oxalidaceae: *Oxalis corniculata, Oxalis strica*

Geraniaceae weeds: *Geranium carolinense, Erodium cicutarium*

Euphorbiaceae weeds: *Euphorbia helioscopia, Euphorbia maculata, Euphorbia humistrata, Euphorbia esula, Euphorbia heterophylla, Acalypha australis*

Malvaceae weeds: *Abutilon theophrasti, Sida spinosa, Hibiscus trionum*

Violaceae weeds: *Viola arvensis, Viola tricolor*

Cucurbitaceae weeds: *Sicyos angulatus, Echinocystis lobata*

Lythraceae weeds: *Lythrum salicaria*

Apiaceae weeds: *Hydrocotyle sibthorpioides*

Asclepiadaceae weeds: *Asclepias syriaca, Ampelamus albidus*

Rubiaceae weeds: *Galium aparine, Galium spurium* var. *echinospermon, Spermacoce latifolia*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea coccinea, Ipomoea quamoclit, Convolvulus arvensis, Calystegia hederacea*)

Boraginaceae weeds: *Myosotis arvensis*

Lamiaceae weeds: *Lamium purpureum, Lamium amplexicaule*

Solanaceae weeds: *Datura stramonium, Solanum nigrum, Solanum americanum, Solanum ptycanthum, Solanum sarrachoides, Solanum rostratum, Solanum aculeatissimum, Solanum carolinense, Physalis angulata, Physalis subglabrata, Nicandra physaloides*

Scrophulariaceae weeds: *Veronica hederaefolia, Veronica persica, Veronica arvensis*

Plantaginaceae: *Plantago asiatica*

Asteraceae weeds: *Xanthium pensylvanicum, Xanthium occidentale, Helianthus annuus, Matricaria chamomilla, Matri-* caria perforata, Chrysanthemum segetum, Matricaria matricarioides, Artemisia princeps, Solidago altissima, Taraxacum officinale, Galinsoga ciliata, Senecio vulgaris, Conyza bonariensis, Conyza canadensis, Ambrosia artemisiaefolia, Ambrosia trifida, Bidens pilosa, Bidens frondosa, Cirsium arvense, Cirsium vulgare, Carduus nutans, Lactuca serriola, Sonchus asper Liliaceae weeds: *Allium canadense, Allium vineale*

Commelinaceae weeds: *Commelina communis, Commelina bengharensis*

Poaceae weeds: *Echinochloa crus-galli, Setaria viridis, Setaria faberi, Setaria glauca, Digitaria ciliaris, Digitaria sanguinalis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromustectorum, Hordeum jubatum, Aegilops cylindrica, Phalaris arundinacea, Phalaris minor, Apera spica-venti, Panicum dichotomiflorum, Panicum texanum, Brachiaria platyphylla, Cenchrus echinatus, Cenchrus pauciflorus, Eriochloa villosa*

Cyperaceae weeds: *Cyperus microiria, Cyperus iria, Cyperus rotundus, Cyperus esculentus, Kyllinga gracillima*

Equisetaceae weeds: *Equisetum arvense, Equisetum palustre* and the like.

In the method of the present invention, one or more kinds of other agrochemicals can be used in combination. Examples of other agrochemicals include insecticides, acaricides, nematocides, fungicides, herbicides, plant growth regulators and safeners.

Examples of other agrochemicals include:

Insecticides: fenthion, fenitrothion, pirimiphos-methyl, diazinon, quinalphos, isoxathion, Pyridafenthion, chlorpyrifos-methyl, vamidothion, malathion, phenthoate, dimethoate, disulfoton, monocrotophos, tetrachlorvinphos, chlorfenvinphos, propaphos, acephate, trichlorphon, EPN, pyraclorfos, carbaryl, metolcarb, isoprocarb, BPMC, propoxur, XMC, carbofuran, carbosulfan, benfuracarb, furathiocarb, methomyl, thiodicarb, cycloprothrin, ethofenprox, cartap, bensultap, thiocyclam, buprofezin, tebufenozide, ethiprole, pyridalyl, clothianidin, dinotefuran, imidacloprid, thiamethoxam, acetamiprid, nitenpyram and thiacloprid.

Acaricides: hexythiazox, pyridaben, fenpyroximate, tebufenpyrad, chlorfenapyr, etoxazole, pyrimidifen, and spirodiclofen.

Nematocides: fosthiazate

Fungicides: captan, IBP, EDDP, tolclofos-methyl, benomyl, carbendazim, thiophanate-methyl, mepronil, flutolanil, thifluzamid, furametpyr, teclofthalam, pencycuron, carpropamid, diclocymet, metalaxyl, triflumizole, azaconazole, bromuconazole, cyproconazole, diclobutrazol, difenoconazole, diniconazole, diniconazole-M, epoxiconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, pefurazoate, prochloraz, azoxystrobin, dimoxystrobin, fluoxastrobin, kresoxim-methyl, metominostrobin, orysastrobin, picoxystrobin, pyraclostrobin, trifloxystrobin, validamycin A, blasticidin S, kasugamycin, polyoxin, fthalide, probenazole, isoprothiolane, tricyclazole, pyroquilon, ferimzone, acibnzolar S-methyl, diclomezine, oxolinic acid, phenazine oxide, TPN and iprodione.

Herbicide: 2,4-D, 2,4-DB, MCPA, MCPB, mecoprop, mecoprop-P, dichlorprop, dichlorprop-P, dicamba, dicamba diglycolamine salt, dicamba-dimethylammonium, dicamba-potassium, dicamba-sodium, bromoxynil, dichlobenil, ioxynil, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, benzobicyclon, dithiopyr, triclopyr, thiazopyr, aminopyralid, clopyralid, dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, tefuryltrione, isoxachlortole, benzofenap, pyrazolynate, pyrazoxyfen, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazaquin, imazethapyr, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glufosinate, glufosinate-ammonium, glufosinate-P, glufosinate-P-sodium, bialafos, anilofos, bensulide, butamifos, paraquat and diquat.

Plant growth regulators (Plants growth regulating active ingredient): hymexazol, paclobutrazol, uniconazole, uniconazole-P, inabenfide, prohexadione-calcium, 1-methylcyclopropene, trinexapac and gibberellins.

Safeners: benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, and oxabetrinil.

EXAMPLES

The present invention will be described more specifically by way of Examples, but the present invention is not limited to these Examples.

In the following description, "ha" means hectare, in other words, 10,000 m².

In the following Examples, herbicidal effect was evaluated by the following "evaluation criteria".

[Evaluation Criteria]

The herbicidal effect was evaluated by the following: comparing the state of budding or growth of test weeds upon examination with that without being treated, and obtaining the ratio of the number of budding or growth of test weeds in a treated sample relative to the number in a non-treated sample; and is indicated by the criteria 0 to 100, where score of the case where the state of budding or growth of test weeds upon examination is completely or substantially the same as the state in the case of no treatment is "0", while score of the case where the test plant is completely dead, or budding or growth is completely suppressed is "100".

Example 1

A plastic pot measuring 255 mm in length, 173 mm in width and 70 mm in height (all of which are inside dimensions) was filled with a field soil, and seeds of soybean (cultivar: Williams 82) and ivyleaf morningglory (*Ipomoea hederacea*) were sown.

On the day of seeding, an isoxaflutole granular wettable powder (a granular wettable powder containing 75% isoxaflutole, trade name: Balance, manufactured by Aventis) and a flumioxazin granular wettable powder (a granular wettable powder containing 51% flumioxazin, trade name: Valor SX, manufactured by Valent USA) were mixed and then the mixture was diluted with water to make the amount of the compounds be in the ratio as shown in Table 1. This water dilution was uniformly sprayed over a surface of the soil in an amount shown in Table 1 using a portable sprayer.

This pot was placed in a greenhouse, followed by rearing. Twenty days after subjecting to a chemical treatment, a herbicidal effect on ivyleaf morningglory (*Ipomoea hederacea*) was evaluated. This test was conducted twice. Among the tests, the amount ratio of the compounds was different from each other. The results are shown in Table 1.

TABLE 1

| Test No. | Amount of chemical[1] (Isoxaflutole + flumioxazin) g/ha | Effect on ivyleaf morningglory (*Ipomoea hederacea*) |
| --- | --- | --- |
| 1-1 | 25 + 13 | 60 |
| 1-2 | 100 + 13 | 95 |

[1]The ratio of chemicals is the same as that of the amounts shown in the column.

Example 2

A plastic pot (pot I) measuring 158 mm in length, 108 mm in width and 70 mm in height (all of which are inside dimensions) and a plastic pot (pot II) measuring 111 mm in inner diameter and 78 mm in height (inside dimension) were filled with a field soil, and seeds of common purslane (*Portulaca oleracea*) were sown in the latter pot (II).

On the day of seeding of common purslane (*Portulaca oleracea*), an isoxaflutole granular wettable powder (a granular wettable powder containing 75% isoxaflutole, trade name: Balance, manufactured by Aventis) and a flumioxazin granular wettable powder (a granular wettable powder containing 51% flumioxazin, trade name: Valor SX, manufactured by Valent USA) were mixed and then the mixture was diluted with water to make the amount of the compounds be in the ratio as shown in Table 2. This water dilution was uniformly sprayed over a surface of the soil filled in the pot I and the pot II in an amount shown in Table 2 using a portable sprayer.

Fourteen days after subjecting a chemical treatment, seeds of soybean (cultivar: Williams 82) were sown in the pot I.

The pot I and the pot II were placed in a same greenhouse, followed by rearing. Twenty-one days after subjecting to a chemical treatment, a herbicidal effect on common purslane (*Portulaca oleracea*) was evaluated. This test was conducted four times. Among the tests, the amount ratio of the compounds was different from each other. The results are shown in Table 2.

TABLE 2

| Test No. | Amount of chemical[1] (Isoxaflutole + flumioxazin) g/ha | Effect on common purslane (*Portulaca oleracea*) |
| --- | --- | --- |
| 2-1 | 1 + 1 | 100 |
| 2-2 | 10 + 1 | 100 |
| 2-3 | 1 + 10 | 100 |
| 2-4 | 10 + 10 | 100 |

[1]The ratio of chemicals is the same as that of the amounts shown in the column.

Example 3

A plastic pot measuring 177 mm in inner diameter and 140 mm in height was filled with a field soil, and seeds of soybean (cultivar: Williams 82) were sown. Three days after sowing, seeds of ivyleaf morningglory (*Ipomoea hederacea*) were sown in the same pot.

Ten days after seeding soybean, i.e., seven days after seeding ivyleaf morningglory (*Ipomoea hederacea*), an isoxaflutole granular wettable powder (a granular wettable powder containing 75% isoxaflutole, trade name: Balance, manufactured by Aventis) and a flumioxazin granular wettable powder (a granular wettable powder containing 51% flumioxazin, trade name: Valor SX, manufactured by Valent USA) were mixed and then the mixture was diluted with water to make the amount of the compounds be in the ratio as shown in Table 3-1. This water dilution was uniformly sprayed over weeds and a surface of the soil in an amount shown in Table 3 using a portable sprayer. This pot was placed in a greenhouse, followed by rearing. Four days after subjecting to a chemical treatment, a herbicidal effect on ivyleaf morningglory (*Ipomoea hederacea*) was evaluated. This test was conducted five times. Among the tests, the amount ratio of the compounds was different from each other.

Besides, a mesotrione suspension (a suspension containing 100 g/L of mesotrione, trade name: Callisto, manufactured by Syngenta) and the above flumioxazin granular wettable powder were mixed and then the mixture was diluted with water to make the amount of the compounds be in the ratio as shown in Table 3-2.

The test was conducted five times in the same manner as mentioned above except that the water dilution of mesotrione and flumioxazin was used. Among the tests, the amount ratio of the compounds was different from each other. The results are shown in Tables 3-1 and 3-2.

TABLE 3-1

| Test No. | Amount of chemical[1] (Isoxaflutole + flumioxazin) g/ha | Effect on ivyleaf morningglory (Ipomoea hederacea) |
|---|---|---|
| 3-1 | 0.5 + 10 | 97 |
| 3-2 | 1 + 1 | 90 |
| 3-3 | 1 + 10 | 99 |
| 3-4 | 10 + 1 | 97 |
| 3-5 | 50 + 1 | 99 |

TABLE 3-2

| Test No. | Amount of chemical[1] (Mesotrione + flumioxazin) g/ha | Effect on ivyleaf morningglory (Ipomoea hederacea) |
|---|---|---|
| 3-1a | 0.5 + 10 | 97 |
| 3-2a | 1 + 1 | 99 |
| 3-3a | 1 + 10 | 99 |
| 3-4a | 10 + 1 | 97 |
| 3-5a | 50 + 1 | 97 |

[1]The ratio of chemicals is the same as that of the amounts shown in the column, in each table.

Example 4

In a plastic pot filled with a field soil, seeds of ivyleaf morningglory (Ipomoea hederacea), velvetleaf (Abutilon theophrasti) and redroot pigweed (Amaranthus retroflexus) are sown. On the day of seeding, isoxaflutole and flumioxazin are mixed and then diluted with water. This water dilution is uniformly sprayed over the weeds mentioned above and a surface of the soil using a portable sprayer. This pot is placed in a greenhouse, followed by rearing. Fourteen days after subjecting to a chemical treatment, seeds of cotton are sown. On fourteen days after sowing of cotton, herbicidal effects on ivyleaf morningglory, velvetleaf and redrroot pigweed are confirmed.

Example 5

The test is conducted in the same manner as Example 4 except that mesotrione is used instead of isoxaflutole. As a result, herbicidal effects on ivyleaf morningglory, vevetleaf and redroot pigweed are confirmed.

Example 6

In a plastic pot filled with a field soil, seeds of seeds of ivyleaf morningglory (Ipomoea hederacea), velvetleaf (Abutilon theophrasti) and redroot pigweed (Amaranthus retroflexus) are sown. Sulcotrione and flumioxazin are mixed and then diluted with water. On the day of seeding, this water dilution is uniformly sprayed over the weeds mentioned above and a surface of the soil using a portable sprayer. This pot is placed in a greenhouse, followed by rearing. Fourteen days after subjecting to a chemical treatment, seeds of cotton and soybean are sown. On fourteen days after sowing of cotton and soybean, herbicidal effects on ivyleaf morningglory, velvetleaf and redrroot pigweed are confirmed.

Example 7

The test is conducted in the same manner as Example 6 except that pyrasulfotole is used instead of sulcotrione. As a result, herbicidal effects on ivyleaf morningglory, vevetleaf and redroot pigweed are confirmed.

Example 8

The test is conducted in the same manner as Example 6 except that bicyclopyrone is used instead of sulcotrione. As a result, herbicidal effects on ivyleaf morningglory, vevetleaf and redroot pigweed are confirmed.

Example 9

The test is conducted in the same manner as Example 6 except that topramezone is used instead of sulcotrione. As a result, herbicidal effects on ivyleaf morningglory, vevetleaf and redroot pigweed are confirmed.

Example 10

The test is conducted in the same manner as Example 6 except that tembotrione is used instead of sulcotrione. As a result, herbicidal effects on ivyleaf morningglory, vevetleaf and redroot pigweed are confirmed.

Example 11

In a plastic pot filled with a field soil, seeds of cotton, ivyleaf morningglory (Ipomoea hederacea), velvetleaf (Abutilon theophrasti) and redroot pigweed (Amaranthus retroflexus) are sown. Isoxaflutole and flumioxazin are mixed and then diluted with water. After emergence of cotton, this water dilution is uniformly sprayed over the weeds mentioned above and a surface of the soil using a portable sprayer.

This pot is placed in a greenhouse, followed by rearing. On fourteen days after sowing, herbicidal effects on ivyleaf morningglory, vevetleaf and redroot pigweed are confirmed.

Example 12

The test is conducted in the same manner as Example 11 except that mesotrione is used instead of isoxaflutole. As a result, herbicidal effects on ivyleaf morningglory, vevetleaf and redroot pigweed are confirmed.

Example 13

In a plastic pot filled with a field soil, seeds of soybean, cotton, ivyleaf morningglory (Ipomoea hederacea), velvetleaf (Abutilon theophrasti) and redroot pigweed (Amaranthus retroflexus) are sown. Sulcotrione and flumioxazin are mixed and then diluted with water. After emergence of soybean and cotton, this water dilution is uniformly sprayed over the weeds mentioned above and a surface of the soil using a portable sprayer.

This pot is placed in a greenhouse, followed by rearing. On fourteen days after sowing, herbicidal effects on ivyleaf morningglory, velvetleaf and redrroot pigweed are confirmed.

Examples 14 to 17

The test is conducted in the same manner as Example 13 except that any one of bicyclopyrone, pyrasulfotole, topramezone and tembotrione is used instead of sulcotrione. As a result, herbicidal effects on ivyleaf morningglory, velvetleaf and redrroot pigweed are confirmed.

INDUSTRIAL APPLICABILITY

The method of the present invention is useful for controlling the soybean or cotton field.

The invention claimed is:

1. A method of controlling weeds in a soybean field, which comprises the step of applying one or more 4-hydroxyphenylpyruvate dioxygenase inhibitory active compounds and flumioxazin in an effective amount to weeds in a soybean field, or a place where weeds would grow in the soybean field, said 4-hydroxyphenylpyruvate dioxygenase inhibitory active compounds being selected from the group consisting of isoxaflutole and mesotrione;
   wherein the 4-hydroxyphenylpyruvate dioxygenase inhibitory active compound and flumioxazin are applied in a weight ratio of 1:0.02 to 1:20.

2. The method according to claim 1, wherein the 4-hydroxyphenylpyruvate dioxygenase inhibitory active compound and flumioxazin are applied in a weight ratio of 1:0.08 to 1:20.

3. The method according to claims 1 or 2, wherein soybean in the soybean field is transgenic soybean.

4. The method according to claims 1 or 2, wherein soybean in the soybean field is herbicide-resistant transgenic soybean.

5. The method according to claim 1 or 2, wherein soybean in the soybean field is 4-hydroxyphenylpyruvate dioxygenase inhibitor-resistant transgenic soybean.

6. The method according to claim 1 or 2, wherein soybean in the soybean field is soybean having one or more genes selected from the group consisting of a gene encoding 4-hydroxyphenylpyruvate dioxygenase exhibiting resistance to a 4-hydroxyphenylpyruvate dioxygenase inhibitor, a gene encoding an enzyme capable of synthesizing homogentisic acid even when 4-hydroxyphenylpyruvate dioxygenase is inhibited by a 4-hydroxyphenylpyruvate dioxygenase inhibitor, a gene capable of excessively expressing 4-hydroxyphenylpyruvate dioxygenase, and a gene encoding prephenate dehydrogenase.

* * * * *